(12) United States Patent
Harris

(10) Patent No.: US 10,552,659 B2
(45) Date of Patent: Feb. 4, 2020

(54) LATENT FINGERPRINT DEVELOPMENT ON POROUS SURFACES

(71) Applicant: Howard A. Harris, Orange, CT (US)

(72) Inventor: Howard A. Harris, Orange, CT (US)

( * ) Notice: Subject to any disclaimer, the term of this patent is extended or adjusted under 35 U.S.C. 154(b) by 163 days.

(21) Appl. No.: 15/731,809

(22) Filed: Aug. 4, 2017

(65) Prior Publication Data

US 2018/0039813 A1 Feb. 8, 2018

Related U.S. Application Data

(60) Provisional application No. 62/494,340, filed on Aug. 4, 2016.

(51) Int. Cl.
*G06K 9/00* (2006.01)
*H05B 6/64* (2006.01)
*A61B 5/1172* (2016.01)

(52) U.S. Cl.
CPC .......... *G06K 9/0008* (2013.01); *A61B 5/1172* (2013.01); *G06K 9/00013* (2013.01); *H05B 6/64* (2013.01)

(58) Field of Classification Search
CPC ...... G06K 9/0008; G06K 9/00; A61B 5/1172; H05B 6/64
See application file for complete search history.

(56) References Cited

U.S. PATENT DOCUMENTS

| | | | | |
|---|---|---|---|---|
| 4,806,380 A | * | 2/1989 | Sato | A61B 5/1172 118/31.5 |
| 2006/0039841 A1 | * | 2/2006 | Rico | A01N 37/16 422/305 |

OTHER PUBLICATIONS

Patton et al. Detection of latent fingermarks on thermal printer paper by dry contact with 1,2-indanedione, Analytical Methods, 2010, 2 pp 631-637. (Year: 2010).*

* cited by examiner

*Primary Examiner* — Kelly M Gambetta
(74) *Attorney, Agent, or Firm* — James F. Kirk

(57) ABSTRACT

The disclosed invention pertains to latent fingerprint development, in general, on absorbent surfaces, and more specifically, to make visible latent finger print images of friction ridge material on porous surfaces thereby facilitating comparison of evidence with known finger print images. The preferred embodiment utilizes a contact dry ninhydrin treatment of porous surfaces which are heated by external electromagnetic radiation, such as that obtained from an ordinary microwave oven, to elicit fingerprint images visible without the need for organic solvents or alternate light sources.

8 Claims, 4 Drawing Sheets

LATENT FINGERPRINT DEVELOPMENT ON POROUS SURFACES

Figure 1:
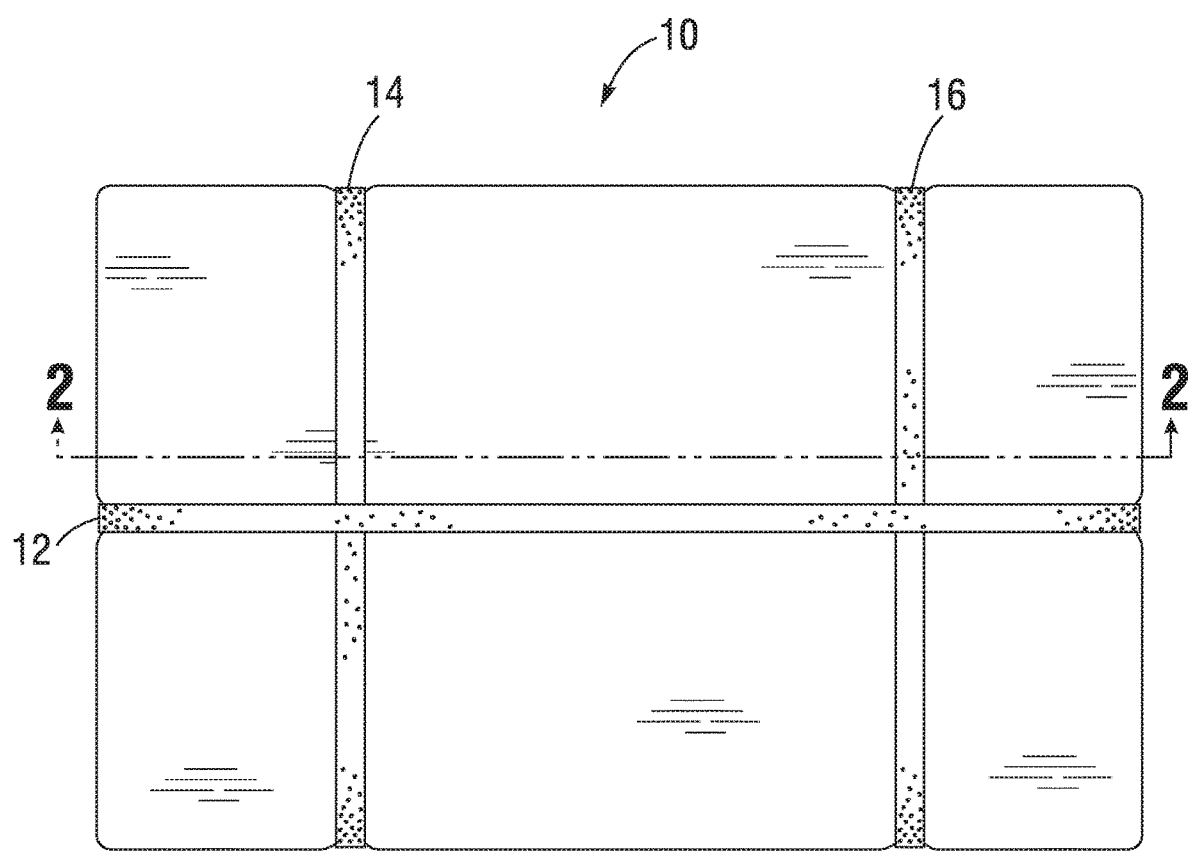

Applicant claims priority from Provisional Patent Application No. 62/494,340 Filed on 4 Aug. 2017.

BACKGROUND—FIELD OF INVENTION

This patent discloses a method (Contact Ninhydrin) of using a suitable absorbent substrate, super-absorbent polymer or other moisture source, and a chemical combination on card stock, containing Ninhydrin and enhancers, to visualize latent fingerprints on the absorbent surfaces (paper). This method utilizes microwave energy in combination with the enumerated components to provide a faster, easier and more reliable method than prior wet chemical methods. Further, minimally trained or lay persons can use the proposed method to obtain high quality and easily observed fingerprints on a variety of absorbent surfaces using no organic solvents.

Visualizing latent images left on absorbent surfaces, most commonly paper, is an important investigative technique used by investigators and fingerprint examiners. For many years a solution of Ninhydrin in acetone was the reagent of choice for visualizing latent prints on absorbent surfaces, since Ninhydrin is quite soluble in acetone and one can easily dissolve more than enough Ninhydrin to make a useful working solution. It is currently more common to dissolve the Ninhydrin in a nonflammable solvent or a hydrocarbon solvent with other additives to help the Ninhydrin dissolve since Ninhydrin is most soluble in polar solvents. The chemical reaction between Ninhydrin and amino acids contained in the fingerprint residue is relatively slow at room temperature. People have tried to accelerate the process by steaming or ironing the latent fingerprint substrate after it was dipped in a Ninhydrin solution to make the reaction go more quickly.

A disadvantage to this as it frequently causes purple color development in the background of the substrate and thereby reduces contrast with the purple color that is formed when amino acids react with the Ninhydrin solution. Therefore, although the reaction proceeds more quickly the fingerprints visualized may not be as highly visible. Polar solvents and also sometimes even many non-polar solvents, will cause problems for Questioned Document examiners because the solvent that is used for the Ninhydrin solution will often cause ink, particularly ballpoint pen ink, to run and one loses clarity in the document. Although commercial or lab prepared Ninhydrin solutions are available, many investigators and fingerprint examiners are not chemists and not comfortable with proper precautions and safety measures when using organic solvents both polar and non-polar.

A little used method that was called "Dry Ninhydrin" has been known for a number of years to avoid the ink running problem. This was done by dipping pieces of paper in a Ninhydrin solution and then, after drying the paper, applying them, usually to both sides of an evidence document, since it is not known which side of the substrate fingerprints are on, and then placing the combination under some weight to improve contact. This combination is then allowed to react in the dark, usually for an extended period of time. One must make these dry Ninhydrin materials to use with the "dry Ninhydrin" method since, as far as we know, they are not available commercially. This method has never been widely used since it is very slow, a minimum of 48 hours is recommended and results are not as reliable as the solution method. We thought we could improve this method by warming or finding a catalyst. Surprisingly, we discovered that if in addition to the Ninhydrin sheets we added a diaper pad that had been dampened to wet the super-absorbent polymer beads in the diaper pad and warm the package, under tension, in a microwave oven one obtained good color development on the substrate with gently heating in about five minutes. We have greatly optimized this novel process as described in the Although commercial or lab prepared Ninhydrin solutions are available, many fingerprint examiners are not chemists and not comfortable with proper precautions and safety measures in using organic solvents both polar and non-polar. A method called "Dry" or as we now prefer to refer to it as "Contact" Ninhydrin has been used for a number of years to avoid the ink running problem. This was done by dipping absorbent pieces of paper in a Ninhydrin solution and then, after the solvent had evaporated, placing the Ninhydrin paper usually on both sides of a evidence document, since it is not known which side of the substrate fingerprints are on, and then placing the combination between two objects and placing them under something heavy to promote contact. The package is then allowed to react in the dark, usually for an extended period of time (forty eight hours or more). One must make these dry Ninhydrin materials to use with the "dry" Ninhydrin method since, as far as we know, they are not available commercially. There are several disadvantages to the "dry" Ninhydrin method as it has been used in the past.

SUMMARY OF THE INVENTION

The method taught in this application for a "Contact Ninhydrin method" utilizes a sandwich containing the basic components necessary for Contact Ninhydrin fingerprint development. The sandwich can use artist board or other low microwave absorbing rigid board (5.5×8.5 in) as the bottom of the sandwich such as polystyrene board. Next a piece of thick filter paper, next a Ninhydrin treated piece of card stock (60-100 lb. paper) treated with Ninhydrin and additives; next fingerprint substrate (normal copy paper with real or synthetic fingerprint material); next another piece of card stock treated with Ninhydrin and additives, next moisture source that can be diaper pads, dampened 3MM filter paper or what we call a "DelaQ" moisture package (see below), next the top of sandwich which can be either another artist board, a piece of rigid polystyrene foam or other rigid plastic boards with low microwave absorbance. The sandwich can be held tightly together with heavy-duty elastic bands.

Benefits Over Prior Art-of Proposed Contact Ninhydrin Method

1. The proposed "contact" Ninhydrin method does not cause the running of most ballpoint pen inks
2. The proposed "contact" Ninhydrin method greatly speeds the Ninhydrin reaction with the amino acids in fingerprints versus the "dry" Ninhydrin method (less than ten minutes versus at least two days)
3. The method does not cause colorization of the substrate background, which makes for better contrast.
4. Ninhydrin sheets are easily prepared, stored, quite stable and readily portable.
5. The development process is free of any organic solvents.
6. The Ninhydrin sheets are easily made in batches with a "green" solvent (ethanol).
7. The Ninhydrin sheets can be used multiple times.
8. The Ninhydrin sheets use card stock thickness, preferably 80-100 lb stock, but otherwise normal paper. Enhancers added to the Ninhydrin sheets are designed to speed the reaction and improve contact between Ninhydrin sheet and substrate. Enhancers reduce the "spottiness" of prints produced using the older "dry" Ninhydrin method.

9. The use of microwave on low power settings heats, but does not color or otherwise charge the substrate. Ninhydrin sheets may become colored but still retain their activity to react with fingerprint material and do not color the substrate even on sub-sequent usage.

10. Although the "dry" Ninhydrin method has been known for a long time it is invariably a very much slower reaction than one obtains when using the "Contact Ninhydrin" method. In fact, the commended development period is 48 hours or more in the dark for the "dry" method 11. The portable moisture source, "DelaQ packets", are stable for an extended period when stored in a high humidity closed container.

The sandwich is placed inside a normal microwave oven set at a low or defrost setting and micro waved for two to five minutes depending on wattage of the oven. The sandwich is removed and allowed to cool for a few minutes before being opened and the substrate being examined. If the prints developed appear weak or spotty the sandwich can be reassembled, with the Ninhydrin sheets each turned over to make contact between the substrate and Ninhydrin sheets in a slightly different area and micro waved again.

A BRIEF DESCRIPTION OF THE DRAWINGS

Figure 2:
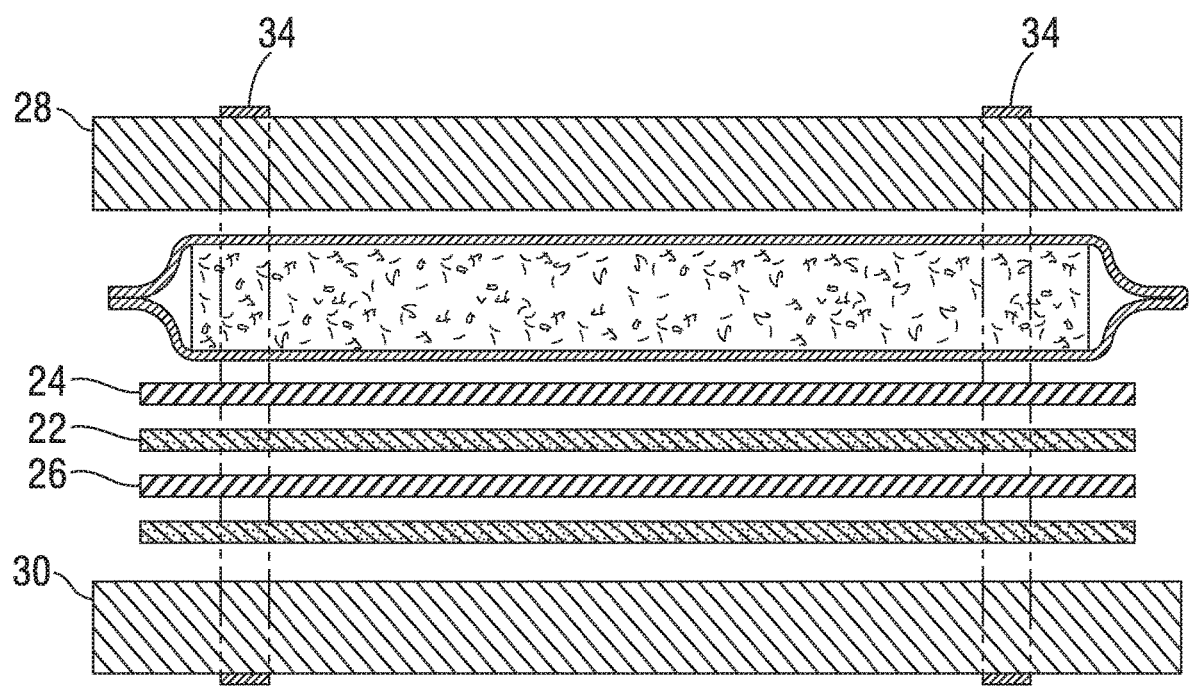
Figure 3:
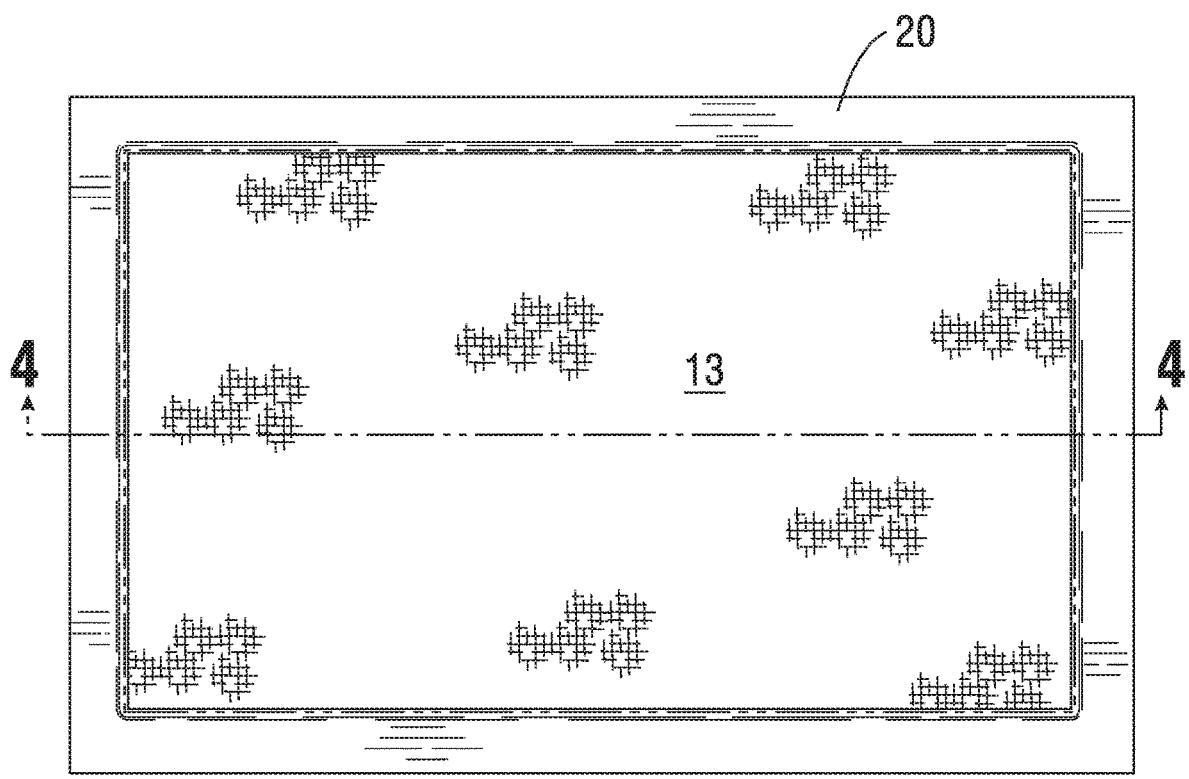
Figure 4:
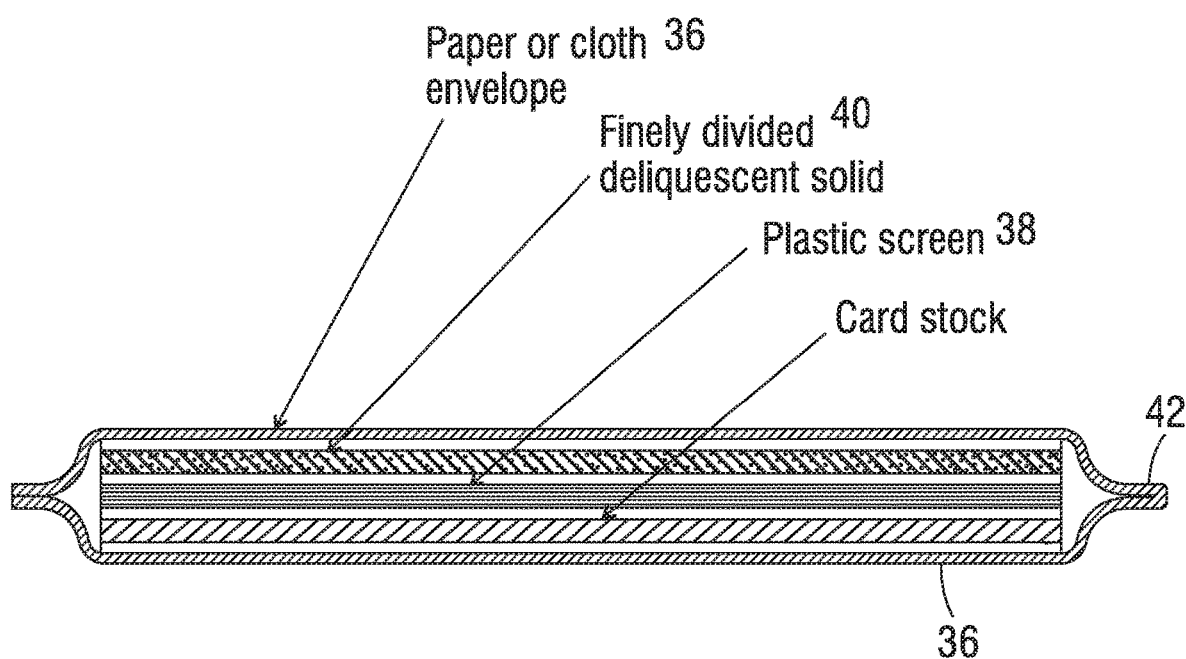

FIG. 1 is schematic illustration of a banded package or sandwich used in the contact dry Ninhydrin process showing elastic bands holding the sandwich together, FIG. 2 is a schematic sectional view of the banded package or sandwich of FIG. 1 taken on section line 2-2 of FIG. 2, FIG. 3 is schematic illustration of a Delaq package containing a deliquescent solid enclosed in a filter paper packet, and FIG. 4 is a schematic sectional view of FIG. 3 taken on section line 4-4 of FIG. 3

DESCRIPTION OF THE INVENTION

FIG. 1, is a schematic showing of an assembled sandwich 10, clamped by elastic bands 12, 14 and 16 and ready for insertion into a microwave.

FIG. 2 is a schematic showing of a sectional view of the sandwich of FIG. 1 with the section being taken on section line 2-2 of FIG. 1.

A delaq 20 package is shown in FIG. 2 under the top polystyrene board 28 and over the top Ninhydrin sheet 24.

1. Sandwich 10 is designed at one half normal letter size (5.5×8.5) to allow it to fit in a normal home-style microwave oven.

2. The following method is disclosed for making Dried Ninhydrin Card Stock. The method is also useful for producing a dried sheet of card stock containing chemicals that rapidly, upon warming react with amino acids in the substrate and produce a strong color and also contains a high boiling liquid that enhances contact between card stock and substrate and catalyzes the chemical reaction. The card stock is prepared by the following steps:

a) Making a solution by dissolving the color producing chemical and an additive that is a nonvolatile liquid in quantities designed to provide rapid reaction between the card stock and substrate when in contact and warned in the presence of moisture. The solvent for the solution is a polar, volatile organic solvent.

b) The card stock is immersed in the solution until saturated with the solution and then removed and the solvent is allowed to evaporate at room temperature.

c) When the card stock has dried, the combination of the reactive chemical and additive provide a medium that enhances contact between the substrate sheet and the card stock and allows visualization of any latent images on the substrate in a short time when subjected to gentle microwave radiation.

3. If fingerprint substrate 22 is full letter size it can be folded in half with one Ninhydrin sheets 24, 26 place inside the folded paper and one inside and outside the folded paper. This will allow all surfaces of the substrate to be developed. Sheets on each side of folded paper will develop the outside of the substrate sheet 22 while the sheet inside will develop inside of the folded sheet.

4. FIG. 3, shows a Moisture source, such as a delaq package 20, can be either diaper pads that have been dampened thoroughly and allowed to surface dry.

FIG. 4 is a schematic sectional view of FIG. 3 taken on section line 4-4 that shows the placement of elements within a Delaq package as described below.

We have developed an excellent portable moisture source, "DelaQ" packet, using a deliquescent solid (chemical drying agent). FIG. 4 shows an 8.5×11 inch piece of #1 filter paper is folded in half to form the outside cover, and a 5.5×8.5 inch piece of plastic window screen inside. A 4-5 gram portion of finely powdered deliquescent solid 40 in the anhydrous form (sodium or magnesium sulfate work well) is spread evenly over the piece of screen leaving an about three quarter inch empty area around the three open sides. A bead of waterproof liquid glue 42 is laid around the three open sides in the open area and the package is closed by pressing the sides together. The glue is allowed to set overnight under some weight. When the glue has set, the package is placed in a high humidity area. A plastic container with a dampened sponge works well, and is allowed to absorb moisture. The initial hydration takes a day or two, but rehydration after use in the microwave is faster.

The combination of the above materials with largely microwave transparent boards to hold the sandwich together tightly with the help of heavy elastic bands, provides a neat package for activation using microwave energy.

The sandwich becomes warm enough to speed the Ruhemann's purple reaction without discoloring the substrate. Everything needed, except for the microwave oven, can be easily transported and can be stored at room temperature for an extended period.

A typical package should contain three to five grams of water absorbed in the superabsorbent polymer beads, but feel dry to the touch. The package can be stored for a considerable time in a humidified plastic container without losing the absorbed water. In the absence of a Delaq package, the moisture can also be provided by using two sheets of heavy filter paper (3MM). One dry sheet is placed in contact with the top Ninhydrin sheet and the other sprayed lightly with water and place in contact with the dry sheet in the sandwich. The third and most convenient method is using a portable moisture source DeleQ moisture packet 20.

The major components of the "Contact Ninhydrin" method are the use of ninhydrin sheets with additives, the use of gentle microwave heating, the presents of additives to improve contact between substrate and ninhydrin and speed the amino acid ninhydrin reaction and the supplying of steam for gently heating the reaction without significantly wetting the substrate.

A cocktail of Ninhydrin, high boiling (non-volatile), polar solvent and acid catalyst is placed on the Ninhydrin sheets by dissolving the desired mixture of materials in a volatile polar solvent. This solution is used to saturate the card stock sheets and then the solvent is allowed to evaporate, leaving a dry to the touch piece of card stock (Ninhydrin sheet) that can be stored in the dark, at room temperature, for an extended period. These sheets can be used multiple times and work particularly well in combination with heat and moisture provided by the rest of the process. The enhancers added to the Ninhydrin sheets add a combination of a layer of highly polar, non-volatile, good solvent for Ninhydrin, and a source of hydrogen ions needed for the Ruhemann's Purple reaction. The enhancers can be liquid polymers, ionic liquids or deep eutectic liquids.

The necessary heating using microwave energy. This function can also be accomplished active areas of diapers, which contain super-absorbent polymer beads embedded in cotton. They can be wetted thoroughly and allowed to surface dry, with the moisture strongly held in the beads. The surface of the pad is dry to the touch, but rapidly releases water vapor when subjected to Microwave energy. The use of the super-absorbent polymer allows one to dampen the pad and keep it for an extended period so it can be used for fingerprint development without immediate dampening. The diaper pads will hold their water for weeks if kept in a humidified (wet sponge) plastic container.

A combination of the above materials and the described action scheme allows one to make the "Contact Ninhydrin" method a rapid and convenient method for visualizing latent fingerprints on a wide variety of absorbent substances. A complete kit of necessary materials for the Ninhydrin development of fingerprints on absorbent surfaces can be about the size of a large sized book.

Disclosed herein is a method for producing a dry to the touch package (Delaq) that contains considerable moisture in the crystal structure of a deliquescent solid that can be released by gentle microwave radiation and can be conveniently recharged with moisture so that it can be used repeatedly as a convent moisture source. The package is composed of:

a) The (Delaq) package is produced using a piece of filter paper or flocked card stock that contains a deliquescent solid that is evenly dispersed over its surface and is enclosed by folding over the paper or cloth to enclose it an outer layer of paper or thin cloth which seals the material into a stable package.

b) The deliquescent solid is held in an evenly dispersed manner by spreading the finely powdered deliquescent solid evenly over a piece of plastic screen or by spreading it evenly over the surface of the flocked side of the card stock.

c) The package is completed by folding a double sized piece of filter paper or thin cloth over the card or screen and the sealing the three open sides with either water resistant glue or, in the case of the cloth, by using an iron-on cloth adhesive.

d) This package can be recharged after use by placing it in a humidor. A simple humidor can be fashioned using an airtight container (plastic, glass or metal) containing a wet sponge or other highly absorbent material which is kept from direct contact with the package by a spacer e) The entire package, card stock, substrate, "Delaq" package, front and back boards and elastic bands, is placed in a microwave oven and heated for a number of minutes with the oven set on "DEFROST". When removed from the oven, it is allowed to cool and then the elastic bands are removed and the individual items taken apart. Whereby any latent friction ridge images on the substrate become viewable and can be easily preserved by photography, scanning or other copying method.

The disclosed method for visualizing friction ridge impressions on absorbent materials that requires no solvents and uses room temperature stable materials that can be readily transported to where ever the substrate materials are and only requires a microwave oven in addition to the readily transported end boards, development cards and Delaq packages.

a) The method requires only two active items in addition to the inert cover boards and elastic bands that hold the sandwich together.

b) Both the active items are dry to the touch and stable for months at room temperature when stored in an envelope.

c) The necessary materials, other than the microwave oven can be places in a briefcase sized travel bag and easily transported to wherever they are needed or stored away for easy access. The disclosed invention and method produces visualization of friction ridge images without colorization of the background as is commonly the case when the substrate is dipped in a solution of the color forming chemical or sprayed with such a solution.

a) Under the conditions of the contact process, the color forming reaction appears to be a surface reaction.

b) After several heating cycles the card stock (Ninhydrin sheet) often takes on some pink coloration, both the substrate containing the friction ridge latent image does not color which maximized the contrast between the image and background of the substrate.

Preferred Embodiment Method One a) Prepare the activated card stock. Cut card stock (80-100 weight) into 5.5 by 8.5 inch pieces. Prepare a solution in denatured alcohol or methyl alcohol by dissolving 4 g of Ninhydrin and 25 g of polyethylene glycol (Tween 80) in 100 ml of the solvent. Submerge pieces of card stock in this solution until saturated and then remove and allow to air dry.

b) Prepare the Delaq package by spreading powdered anhydrous Magnesium Sulfate evenly over a 5×8.25 inch piece of plastic screen that is over the bottom half of an 8.5×11 inch piece of filter paper. The package is completed by folding the top half of the filter paper over the bottom half and screen and the sealing the three open sides with a water-resistant glue. This package should be placed under some weight until the glue has completely dried.

c) The end boards are 4 inch thick and 5.5×8.5 inch rigid polyethylene sheet.

d) Prepare a sandwich by placing a sheet of activated card stock on the plastic board, placing the substrate on the card stock. If the substrate is larger than 5.5×8.5 inch fold it in half and place an activated card stock sheet inside the folded substrate. Follow that with another card stock sheet and make sure that these materials are in close contact and then place a delaq package over the card stock and finally cover with the other polyethylene board. This sandwich is then held tightly together with four rubber bands two on each side. The sandwich is now ready for microwaving. It is placed in a microwave oven set to the "defrost mode" and microwaved for about 3.5 minutes. The sandwich is then allowed to cool for at least five minutes before opening the sandwich and examining the substrate for any visualized friction ridge images.

e) The sandwich can contain as many as three different substrates each with activated card stocks on both sides. The card stocks can be used at least five times without losing any of its activity and the Delaq package must be regenerated after use by placing it in a high humidity chamber and it can be reused many times.

Preferred Embodiment Method Two a) Prepare the activated card stock. Cut card stock (80-100 weight) into 5.5 by 8.5 inch pieces. Prepare a solution in methyl alcohol by dissolving 4 g of Ninhydrin and 25 g of a deep eutectic liquid made from lactic acid and dextrose in 100 ml of the solvent. Submerge pieces of card stock in this solution until saturated and then remove and allow to air dry.

b) Prepare the Delaq package by spreading powdered anhydrous Magnesium Sulfate evenly over a 5×8.25 inch piece of flocked card stock that is over the bottom half of an 8.5×11 inch piece of thin cotton cloth. The package is completed by folding the top half of the fabric over the bottom half and then sealing the three open sides with an iron-on adhesive for bonding cloth. This package should be placed under some weight until the fused adhesive has cooled.

c) The bottom end board is a 5.5×8.5 inch artist board and the top end board is a 5.5×8.5 inch piece of polystyrene board.

d) Prepare a sandwich by placing a sheet of activated card stock on the bottom board, placing the substrate on the card stock. If the substrate is larger than 5.5×8.5 inch, fold it in half and place an activated card stock sheet inside the folded substrate. Follow that with another card stock sheet and make sure that these materials are in close contact and then place a Delaq package over the card stock and finally cover with the polystyrene board. This sandwich is then held tightly together with four rubber bands, two on each side. The sandwich is now ready for microwaving. It is placed in a microwave oven set to the "defrost mode" and microwaved for about 3.5 minutes. The sandwich is then allowed to cool for at least five minutes before opening the sandwich and examining the substrate for any visualized friction ridge images.

e) The sandwich can contain as many as three different substrates each with activated card stocks on both sides. The card stocks can be used at least five times without losing any of its activity and the Delaq package must be regenerated after use by placing it in a high humidity chamber. It can be reused many times.

Preferred Embodiment Method Three a) Prepare the activated card stock. Cut card stock (80-100 weight) into 5.5 by 8.5 inch pieces. Prepare a solution in denatured alcohol by dissolving 4 g of Ninhydrin and 25 g of Tween 80 in 100 ml of the solvent. Submerge pieces if card stock in this solution until saturated and then remove and allow to air dry.

b) Prepare the Delaq package by spreading powdered anhydrous Magnesium Sulfate evenly over a 5×8.25 inch piece of flocked card stock that is over the bottom half of an 8.5×11 inch piece of thin cotton cloth. The package is completed by folding the top half of the fabric over the bottom half and then sealing the three open sides with an iron-on adhesive for bonding cloth. This package should be placed under some weight until the fused adhesive has cooled.

c) The bottom and top end boards are 5.5×8.5 inch pieces of polystyrene board.

d) Prepare a sandwich by placing a sheet of activated card stock on the bottom board, placing the substrate on the card stock. If the substrate is larger than 5.5×8.5 inches fold it in half and place an activated card stock sheet inside the folded substrate. Follow that with another card stock sheet and make sure that these materials are in close contact and then place a Delaq package over the card stock and finally cover with the polystyrene board. At this point another substrate can be added and topped with an activated card stock sheet. This sandwich is then held tightly together with four rubber bands, two on each side. The sandwich is now ready for microwaving. It is placed in a microwave oven set to the "defrost mode" and microwaved for about 3.5 minutes. The sandwich is then allowed to cool for at least five minutes before opening the sandwich and examining the substrate for any visualized friction ridge images.

e) The sandwich can contain as many as three or four different substrate sheets each with activated card stock on both sides. The activated card stock cards can be used at least five times without losing any of its activity and the Delaq package must be regenerated after use by placing it in a high humidity chamber. It can be reused many times.

To demonstrate the sensitivity of the Contact Ninhydrin method we have developed sensitivity sheets. To make a sensitivity sheet an individual presses the same finger across a sheet of paper four times with out adding any additional sweat. The first impression will have the most fingerprint material (sweat) and each of the next three will have less. This can be repeated with other fingers to provide additional samples. After Contact Ninhydrin treatment one will see four fingerprints in each row with diminishing intensity. This shows that even very weak fingerprints (three and four) are visualized in most case. Thus the technique will work even on quite weak (very small amount of sweat) casework latent prints.

The technician that uses the "Contact Ninhydrin" developed latent prints on paper avoids the use of a wet bath to immerse the target documents, and a large volume of potentially hazardous and flammable materials. Variations in fluid concentration may adversely affect print recovery results. The disclosed dry ninhydrin process obviates or mitigates all these limitations.

Baby diapers contain PAA bead impregnated in fibers is found in ordinary baby diapers or from crystals. The PAA or Poly Acrylic Acid stabilized within the fiber matrix absorbs copious amounts of water which can be released as steam upon suitable heating, preferably using microwave energy.

FIG. 2 shows the assembled "contact" Ninhydrin sandwich used in the development process. The target paper (substrate) 22 is shown in the center, surrounded by a top and bottom Ninhydrin sheets 24, 26 respectively, covered by PAA-H20 (diaper pad) media, covered by top and bottom artist and polystyrene boards respectively 28, 30 and secured in place using non-ferrous clamps in the form of elastic bands 32, 34. Non-ferrous materials are required for use in a microwave oven to mitigate energy diversion and sparking. A Delaq package 36 is shown beneath the top polystyrene board 28 and the top Ninhydrin Sheet 24

In another test, a test sheet was stamped with synthetic fingerprint material solution to simulate fingerprint residue. The latent stamp images sheet was then written with six different ball point pens. After the Contact Ninhydrin"

development process, there was no discernable effect of the "contact" Ninhydrin process on the ball point ink.

I claim:

1. A dry ninhydrin method for rapidly visualizing latent friction ridge images left by contact of skin on an absorbent surface of a substrate comprising steps:
   a) providing a first sheet of card stock that has been previously saturated with a solution of chemicals and which has been allowed to dry,
   b) covering a first surface of the absorbent surface of the substrate with the first sheet of card stock,
   c) covering the first sheet of card stock with a Delaq package that is dry to the touch and that will provide a moist atmosphere when subjected to microwave radiation,
   d) arranging the Delaq package, the card stock and substrate into a stack,
   e) providing a first and second board, each board having at least one flat surface,
   f) positioning the stack between opposing flat surfaces of the first and second boards and
   g) clamping the boards, together with at least one elastic band to form a banded package,
   h) placing the banded package in a microwave oven and subjecting the banded package to microwave radiation to provide a humid atmosphere and heat and allowing time to pass to allow the substrate to absorb moisture,
   i) removing the banded package from the oven and allowing the banded package to cool before removing the elastic bands.

2. The dry ninhydrin method of claim 1 wherein step a) is amended to be:
   a) provide a first and a second sheet of card stock, each of which has been has been previously soaked in a solution containing ninhydrin, a chemical that reacts with amino acids from fingerprints to produce a purple color image that visualizes the finger print on the substrate and which has been allowed to dry; and
   replace step b) with the following step b):
   b) cover a first surface of the substrate with the first sheet of card stock, and cover the second surface of the substrate with the second sheet of card stock.

3. The dry ninhydrin method of claim 1 wherein step a) is amended to be:
   a) providing a first sheet of card stock that has been previously soaked in and saturated with a solution of chemicals containing ninhydrin that have been allowed to dry.

4. The dry ninhydrin method of claim 1 wherein step c) is amended to be:
   c) covering the first sheet of card stock with a Delaq package that made with the steps comprising:
   c-1) providing a sheet of card stock with a flocked side,
   c-2) providing finely powdered deliquescent solid,
   c-3) spreading the finely powdered deliquescent solid evenly over the flocked side of the card stock,
   c-4) folding a double sized piece of filter paper or thin cloth over the card-stock and the sealing the three open sides with either water resistant glue or, in the case of the cloth, by using an iron-on cloth adhesive.

5. A dry ninhydrin method for rapidly visualizing latent friction ridge images comprising the steps of:
   a) providing a first and a second sheet of flat card stock, each of which has previously been soaked in a solution containing ninhydrin and dried,
   b) providing a Delaq package,
   c) placing a substrate between the first and second sheet of card stock,
   e) positioning the Delaq package on top of the second sheet of card stock to form a stack,
   f) positioning the sandwich between two boards that readily pass microwave energy and,
   g) clamping the sandwich between the two boards to form a banded package,
   h) placing the banded package in a microwave oven and heating the package on a defrost setting to enable the Delaq package to provide a moist environment that penetrates the first and second card-stock and the substrate.

6. The dry ninhydrin method claim 5 wherein step b) is amended to be:
   b) providing a Delaq package made with the following steps:
   b-1) providing a sheet of card stock,
   b-2) provide a sheet of plastic screen that covers the sheet of card stock and attach the sheet of plastic screen to the card stock,
   b-3) providing finely powdered deliquescent solid,
   b-4) spreading the finely powdered deliquescent solid evenly over the plastic screen on the card stock, providing a sheet of card stock with a flocked side,
   b-5) folding a double sized piece of filter paper or thin cloth over the card-stock and then sealing the three open sides with either water resistant glue or, in the case of the cloth, by using an iron-on cloth to form the delaq package
   b-6) if not previously charged with moisture, placing the delaq package in a humidor to charge the deliquescent solid crystals with water.

7. The dry ninhydrin method claim 5 wherein step g) is amended to be:
   g) clamping the sandwich between the two boards to form a banded package by:
   12-a) wrapping the stack with low microwave absorbing plastic sheets can also be used as the top or bottom of the banded package, and
   12-b using elastic bands to immobilize the elements of the sandwich between the boards,
   a) providing a first and a second sheet of flat card stock, each of which has previously been soaked in a solution containing ninhydrin and dried.

8. The dry ninhydrin method claim 5 where in step a) amended to comprise:
   a) providing a first and a second sheet of flat card stock, each of which has previously been soaked in a solution containing ninhydrin and dried by starting with the step:
   13-a) dissolving the color producing chemical in a polar, volatile organic solvent,
   13-b) adding an additive to the solution that is a nonvolatile liquid in quantities designed to provide rapid reaction between the card stock and substrate when the additive is in contact with the substrate and warmed in the presence of moisture,
   13-c) immersing the card stock in the solution until saturated with the solution, and
   13-d) removing the card stock from the solution and allowing the solvent to evaporate at room temperature whereby, after card stock has dried, the combination of the reactive chemical and additive provide a medium that enhances contact between the substrate sheet and the card stock and allows visualization of any latent images on the substrate in a short time when subjected to gentle microwave radiation.

* * * * *